United States Patent
Schweikard et al.

(10) Patent No.: US 7,260,426 B2
(45) Date of Patent: Aug. 21, 2007

(54) METHOD AND APPARATUS FOR TRACKING AN INTERNAL TARGET REGION WITHOUT AN IMPLANTED FIDUCIAL

(75) Inventors: Achim Schweikard, Hamburg (DE); John R. Adler, Stanford, CA (US)

(73) Assignee: Accuray Incorporated, Sunnyvale, CA (US)

(*) Notice: Subject to any disclaimer, the term of this patent is extended or adjusted under 35 U.S.C. 154(b) by 0 days.

(21) Appl. No.: 10/293,216

(22) Filed: Nov. 12, 2002

(65) Prior Publication Data

US 2004/0092815 A1    May 13, 2004

(51) Int. Cl.
*A61B 5/00*    (2006.01)
(52) U.S. Cl. .................. 600/407; 600/410; 600/411; 600/425; 600/427; 600/428; 600/437; 600/534; 600/595
(58) Field of Classification Search ................ 600/425, 600/426, 428, 427, 410, 411, 413, 414, 407, 600/437, 529, 534, 595; 378/69; 128/922; 382/128
See application file for complete search history.

(56) References Cited

U.S. PATENT DOCUMENTS

| | | | | |
|---|---|---|---|---|
| 5,067,494 A | * | 11/1991 | Rienmueller et al. | 600/428 |
| 5,207,223 A | * | 5/1993 | Adler | 600/427 |
| 6,144,875 A | * | 11/2000 | Schweikard et al. | 600/427 |
| 6,370,419 B1 | * | 4/2002 | Lampotang et al. | 600/427 |
| 6,501,981 B1 | | 12/2002 | Schweikard et al. | 600/427 |
| 6,633,775 B1 | * | 10/2003 | Bernard | 600/428 |
| 6,690,965 B1 | | 2/2004 | Riaziat et al. | 600/428 |

OTHER PUBLICATIONS

PCT Written Opinion, mailed Feb. 1, 2006, International Application No. PCT/US03/35801, International Filing Date Nov. 12, 2003, 5 pages.

* cited by examiner

*Primary Examiner*—Ruth S. Smith
(74) *Attorney, Agent, or Firm*—Blakely, Sokoloff, Taylor & Zafman LLP

(57) ABSTRACT

A method and apparatus for locating an internal target region during treatment without implanted fiducials is presented. The method comprises producing a plurality of first images that show an internal volume including the internal target region, then producing a live image of the internal volume during treatment and matching this live image to one of the plurality of first images. Since the first images show the internal target region, matching the live image to one of the first images identifies the position of the target region regardless of whether the second image itself shows the position of the target region. The first images may be any three-dimensional images such as CT scans, magnetic resonance imaging, and ultrasound. The live image may be, for example, an x-ray image. The invention may be used in conjunction with a real-time sensor to track the position of the target region on a real-time basis.

46 Claims, 10 Drawing Sheets

SYSTEM BLOCK DIAGRAM

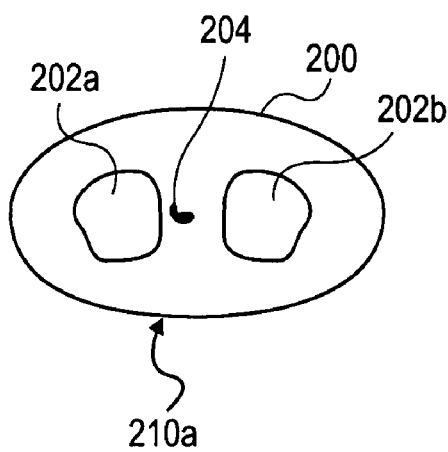
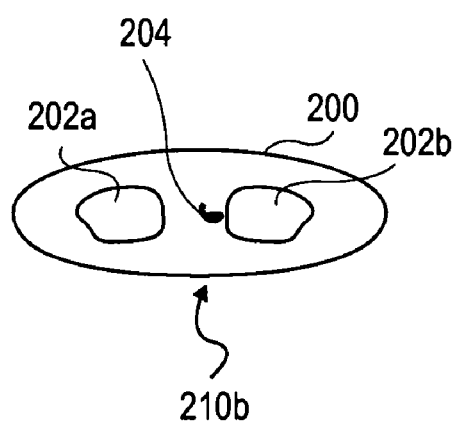
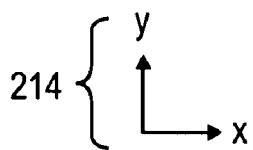
FIG. 5  FIG. 6

METHOD AND APPARATUS FOR TRACKING AN INTERNAL TARGET REGION WITHOUT AN IMPLANTED FIDUCIAL

BACKGROUND OF THE INVENTION

This invention relates generally to an apparatus for improving the accuracy and efficacy of surgical treatments and more particularly to tracking the location of the target region that is displaced during the treatment due to respiratory and other patient motions.

Various treatments require accurate tracking of the location of a target region in order to apply or deliver the treatment to the target region. In radiation therapy and radiosurgery, for example, a tumor may be destroyed by a beam of ionizing radiation that kills the cells in the tumor. As it is desirable to direct the radiation beam only to the tumor and not to the healthy tissues surrounding the tumor, accurate aiming of the beam at the tumor is of paramount importance in radiation treatments. The goal is to focus a high dose of radiation to the tumor while minimizing the exposure of the surrounding healthy tissue to radiation. For adequate distribution of radiation dosage to the tumor, the direction of the radiation beam is typically adjusted during the treatment to track the tumor.

The most advanced modern radiosurgery systems, such as the Cyberknife System of Accuray, Inc., use stereo online x-ray imaging during treatment to enhance the accuracy of radiation treatment. The position of the patient's bony landmarks (e.g., a skull) can be determined with high accuracy by using the Cyberknife stereo x-ray camera system. Thus, this highly accurate x-ray camera system can be used to treat a target region if the position of the target region relative to a bony landmark remains constant. However, this x-ray camera system cannot be used to determine the position of a target region if the position of the target region relative to a bony landmark changes because the target, e.g., a tumor, is generally not visible in x-ray images. For example, a target region in a patient's abdomen or chest cannot be treated with this method alone.

While accurate aiming of the beam is not difficult when the tumor is in a body part that does not move, such as the brain, aiming becomes a challenge when the tumor is in or near a body part that moves, such as the lungs. A tumor located near the lungs moves as the patient inhales and exhales, necessitating continuous adjustment of the radiation beam direction. As the change in the position of the tumor does not necessarily correlate with the change in the position of an external surface of the patient, a tumor cannot be easily tracked based on external measurements alone. For example, placing external sensors on a patient's chest and tracking the movement of the sensors does not provide accurate information about the position of the tumor inside the chest cavity because a certain soft tissue structure may move in one direction while bones move in another direction. Nor can the tumor be located with x-ray systems, because in most cases, neither the target region nor the surrounding soft tissues are visible in the x-ray images. The two-dimensional nature of x-ray images compromises the accuracy with which the radiation is applied to the target region. Moreover, even if x-ray provided accurate enough data, real-time tracking of target region cannot be performed with x-ray imaging alone because of the excess radiation that the patient would be exposed to.

Attempts to improve the tracking accuracy of a target region include use of an internal fiducial. U.S. Pat. No. 6,144,875, for example, discloses a method for tracking a target region by implanting small gold markers that are visible in x-ray images into a patient's abdomen prior to radiation treatment. Once the internal fiducials are implanted, they are periodically imaged with a stereo x-ray camera system so that their positions are accurately determined. Based on the position of the markers, the position of the tumor can be accurately determined.

Unfortunately, use of internal fiducials in the above manner has its disadvantages. First, the x-ray imaging process is too slow and too invasive to track the respiration motion in real-time. The x-ray system allows the location of a tumor to be determined only at certain time intervals, e.g., every 10 seconds, and not continuously. Second, the implanting of the fiducials is an invasive and expensive procedure because the procedure usually takes place under the surveillance of a computer tomography (CT) device and in the presence of a surgeon. The required presence of the surgeon not only drives up the cost of the procedure for the patient but also exposes the surgeon to ionizing radiation. Furthermore, there is a real risk of complications that could result from the fiducial placement.

For the above reasons, it is desirable to provide an apparatus and method for accurately tracking a target region in a patient without the use of internal fiducials, and it is to this end that the present invention is directed.

SUMMARY OF THE INVENTION

A method and apparatus for locating an internal target region during treatment without using implanted fiducials is presented. The method comprises producing a plurality of first images that each shows an internal volume including the internal target region, then producing a live image of the internal volume during treatment and matching this live image to one of the plurality of first images. Since the first images show the internal target region, matching the live image to one of the first images identifies the position of the target region regardless of whether the second image itself shows the position of the target region. The first images may be any three-dimensional images such as CT scans, magnetic resonance imaging, and ultrasound. The live image may be, for example, an x-ray image.

The invention may be used in conjunction with one or more real-time sensors to track the position of the target region on a real-time basis. In order to achieve real time tracking, the signal from the real-time sensor is correlated with the position of the target region. The correlation model is produced by simultaneously taking an x-ray and reading the signal from the real-time sensor, then using the x-ray to identify the best-matching three-dimensional image that shows the target position. Once the correlation is established, the position of the target region can be tracked real time during treatment by reading the signal from the real-time sensor almost continuously.

BRIEF DESCRIPTION OF THE DRAWINGS

FIG. 5 schematically depicts a position of a target region at point A in the respiration cycle;

FIG. 6 schematically depicts a position of a target region at point B in the respiration cycle;

DETAILED DESCRIPTION OF A PREFERRED EMBODIMENT

Figure 1:
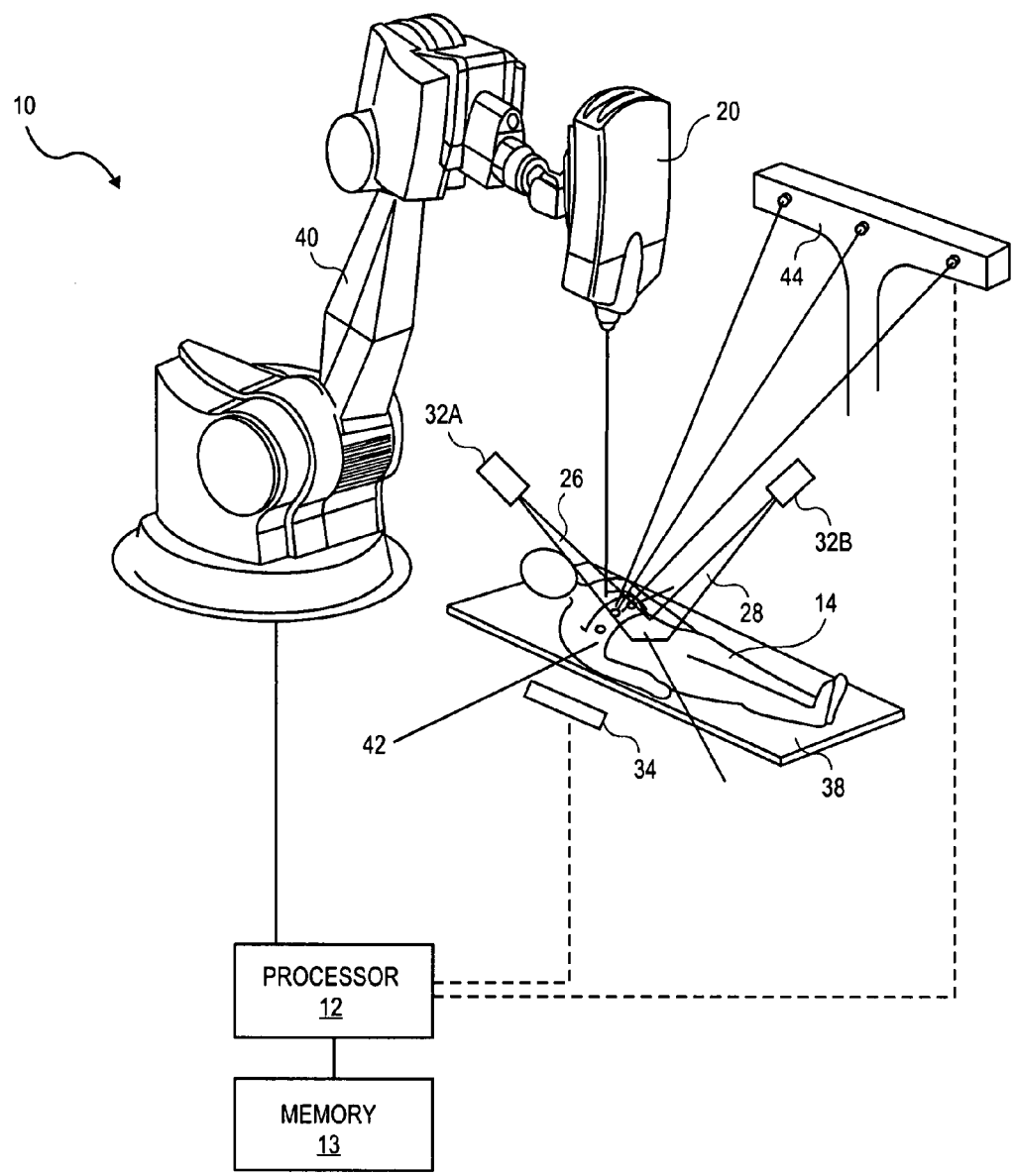
FIG. 1 depicts an example of a radiosurgical treatment system that may be used with the present invention.

The invention is particularly applicable to an apparatus and method for directing a radiation beam towards an internal target region without implanting an internal fiducial in or near the target region to determine its location, and it is in this context that the invention will be described. It will be appreciated, however, that the apparatus and method in accordance with the invention has greater utility, such as to other types of medical procedures with other types of medical instruments, such as positioning biopsy needles, ablative, ultrasound or other focused energy treatments, or positioning a laser beam for laser beam treatment. Prior to describing the invention, a typical radiosurgery device will be described to provide a better understanding of the invention.

As used herein, a "target region" is the region to which a treatment (e.g., radiation) is to be directed. A target region is located in a "relevant volume," which refers to an internal region surrounding the target region, and which may include bones and soft tissues around the target region.

The method according to the invention includes steps that may be executed prior to treatment and steps that are executed during treatment. Prior to treatment, a series of at least two CT scans are taken or computed. Each CT scan corresponds to a particular point in the respiratory cycle of the patient. Each of the series of CT scans may be an actual CT scan or a combination of actual CT scans and computer-generated intermediate CT images. In order to generate intermediate CT images, at least two CT scans are first taken. Then, synthetic deformation images are computed from the actual CT scans. Each CT scan and computer-generated CT image shows the target region. This target region may be marked prior to treatment. A set of digitally reconstructed radiographs (DRRs) is computed for each CT scan and/or computer-generated CT image. Each DRR shows the target region from a particular angle.

During treatment, live stereo x-ray images are taken periodically, e.g., once every 10 seconds. The target region may not be clearly visible in the x-ray images. However, the exact location of the target region can be determined by comparing each live x-ray image with the set of DRRs, finding the DRR that best matches the live x-ray image, and identifying the CT scan or CT image from which the DRR was generated. The CT scan or CT image shows the target region and hence the position of the target region. Based on the viewing angle associated with the best-matching DRR, the exact angle or translational shift the patient was in when the live x-ray image was taken is also determined. Using the DRRs, both a translational/rotational shift of the patient's body and the current respiratory state of the patient may be inferred from the live x-ray images. No fiducial needs to be implanted for this procedure, which only requires x-ray imaging during treatment.

Since x-ray imaging alone may be too slow for detecting fast respiration, the fiducial-less target tracking method according to the invention may be combined with real-time sensors in order to track the target region real time. Real-time sensors may be external markers that are coupled to a patient's body part that moves when the target region moves but not necessarily in the same direction or to the same degree. In order to use real-time sensors, a correlation model correlating signals from the real-time sensors with the position of the target region is generated, preferably prior to treatment. The correlation model is generated by taking an x-ray image of the target region and reading the signal from the real-time sensor simultaneously, then using the x-ray image to identify the best-matching DRR and the associated CT scan or CT image. Since the real-time sensor was read at the same time the x-ray image was taken, the CT scan or the CT image identifies the position of the target region at the time the signal was read from the real-time sensor. After a set of data points are taken, the position of the target region can be correlated with the signal reading from the real-time sensor. This pre-treatment correlation procedure is similar to the live fiducial-less target tracking method that is executed during treatment in that an x-ray image is matched up with a DRR to identify the position of the target region. This correlation procedure differs from the live target region tracking that is done during treatment in that the signal from the real-time sensor is read at the same time an x-ray image is taken. Once the correlation model is established, the position of the target region can be inferred from the real-time sensor signals. As real-time sensor signals are easily obtained and can be read more frequently than x-ray images can be processed, use of a real-time sensor allows the target region to be tracked almost continuously, or real-time. Further details of the correlation procedure are provided in U.S. Pat. No. 6,144,875, which is incorporated herein in its entirety.

FIG. 1 depicts an example of a stereotaxic radiation treatment device 10. The radiation treatment device 10 may include a data processor 12, such as a microprocessor, and a memory unit 13 which may store image data and mathematical data pertaining to a target region inside a patient 14. The image data may be loaded into the data processor either prior to treatment or during the surgical procedure. The radiation treatment device 10 may also include a beaming apparatus 20 which, when activated, emits a collimated surgical ionizing beam directed at a target region inside patient 14. The collimated surgical ionizing beam may have sufficient strength to cause the target region to become necrotic. A variety of different beaming apparatus may be used which generate an ionizing radiation or heavy particle beam such as a linear accelerator and preferably an x-ray linear accelerator. Such an x-ray beaming apparatus is commercially available. The beaming apparatus may be activated by the operator using a switch (not shown) that is connected to the beaming apparatus 20.

The radiation treatment device 10 may also include a stereo x-ray imaging apparatus for passing a first diagnostic beam 26 and a second diagnostic beam 28 through an internal target region. The diagnostic beams may be positioned at a predetermined non-zero angle with respect to each other. The diagnostic beams may be generated by a first x-ray generator 32a and a second x-ray generator 32b, respectively. An image receiver 34 may receive the diagnostic beams 26, 28 to generate an image from the diagnostic beams which is fed into the microprocessor 12 so that the diagnostic images may be compared to the three-dimensional image. In some embodiments, two separate receivers may each receive one the diagnostic beams 26 and 28.

The radiation treatment device 10 may also include a device for adjusting the relative positions of the beaming apparatus 20 and the patient 14 so that the ionizing beam is continuously focused on the target region. In the particular radiation treatment device that is shown, the positioning of the beaming apparatus relative to the patient may be altered by a processor controllable robotic arm mechanism 40 and/or a moveable operating table with a tilting top 38. The robotic arm mechanism permits the beaming apparatus to be moved freely about the patient's body including up, down, longitudinally along or laterally along the body of the patient.

The radiation treatment device 10 may also include a real-time sensing system for monitoring an external movement of the patient 14. The real-time sensing system includes one or more real-time sensors 42 that are coupled to an external body part of the patient 14 and a sensor reader 44 that takes a reading from the real-time sensors 42 periodically. Readings of the real-time sensors 42 indicate the movement of an external body part of the patient 14. This real time sensing system may be any system that can be used for correlating the real-time sensors 42 to respiration pattern with a response/reactivation time of less than 250 ms. Some commercially available sensors that may be used as the real time sensor 42 include infrared tracking systems made by Northern Digital, Inc. (Ontario, Canada), force sensors, air flow meters, strain gauges, laser range sensors, and a variety of sensors based on other physical principles such as haptic, acoustic/ultrasound, magnetic, mechanical or optical principles. Alternatively, the current state of respiration may be measured by viewing video images of the chest and/or abdomen movement, or sensing the flow of air or temperature emulating from the mouth and/or nose of the patient 14. The real-time sensing system is coupled to the processor 12 so that the processor 12 can use the readings of the real-time sensors 42 to establish a correlation.

Figure 2:
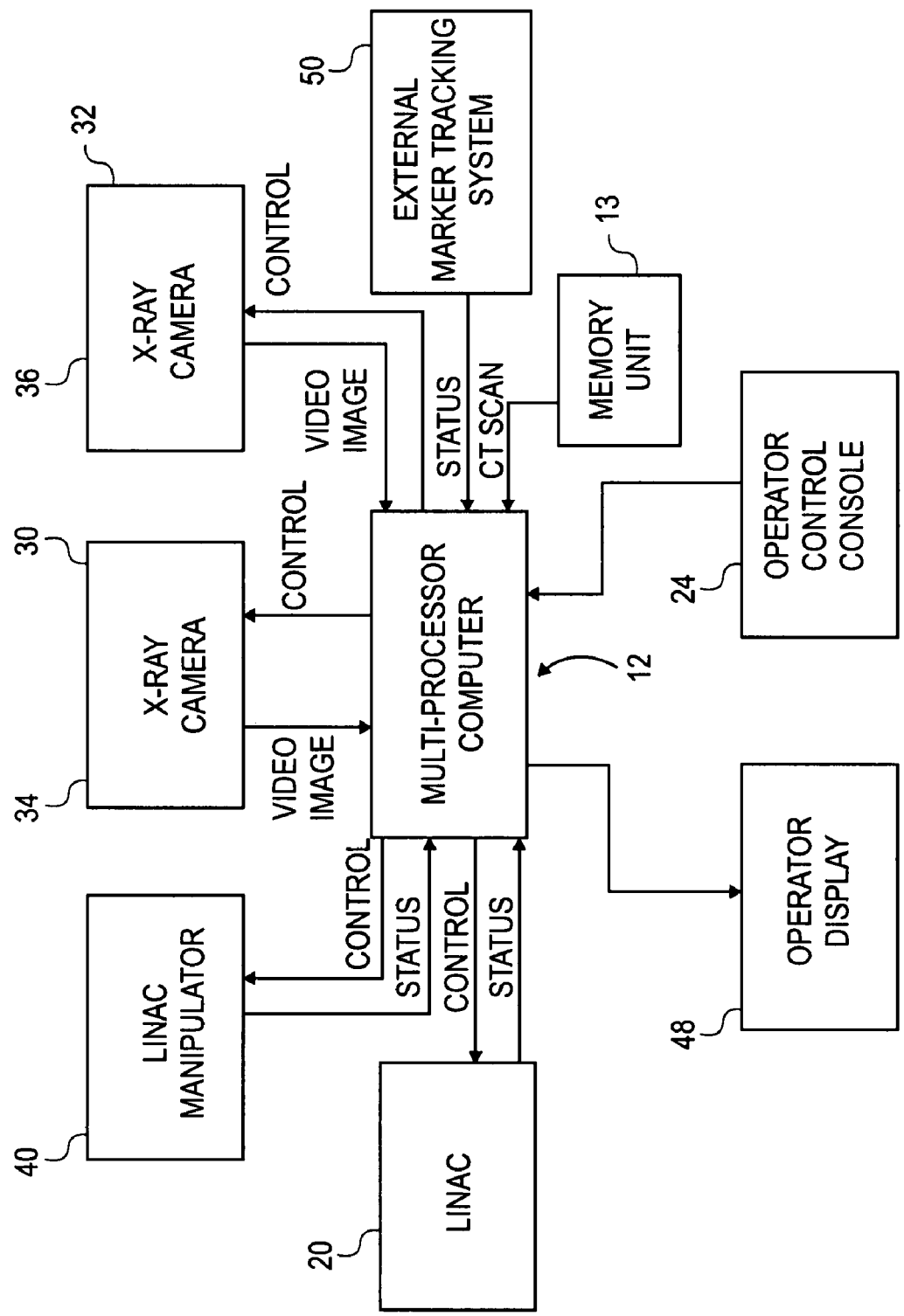
FIG. 2 is a block diagram depicting the treatment system of FIG. 1.

FIG. 2 is a block diagram of the radiation treatment device 10 including the microprocessor 12, the memory unit 13 (e.g., a tape drive), the beaming apparatus 20, the robotic arm 40, the x-ray cameras 30, 32, 34 and 36, and the operator control console 24 as described above. In addition, the device 10 may include an real-time sensor tracking system 50 to track the position of an real-time sensor attached to the skin of patient 14. The device 10 may also include an operator display 48 for tracking the progress of the treatment and controlling the treatment. Any further details of the radiosurgery device may be found in U.S. Pat. No. 5,207,223 which is owned by the assignee of this application and which is incorporated herein by reference.

Figure 3:
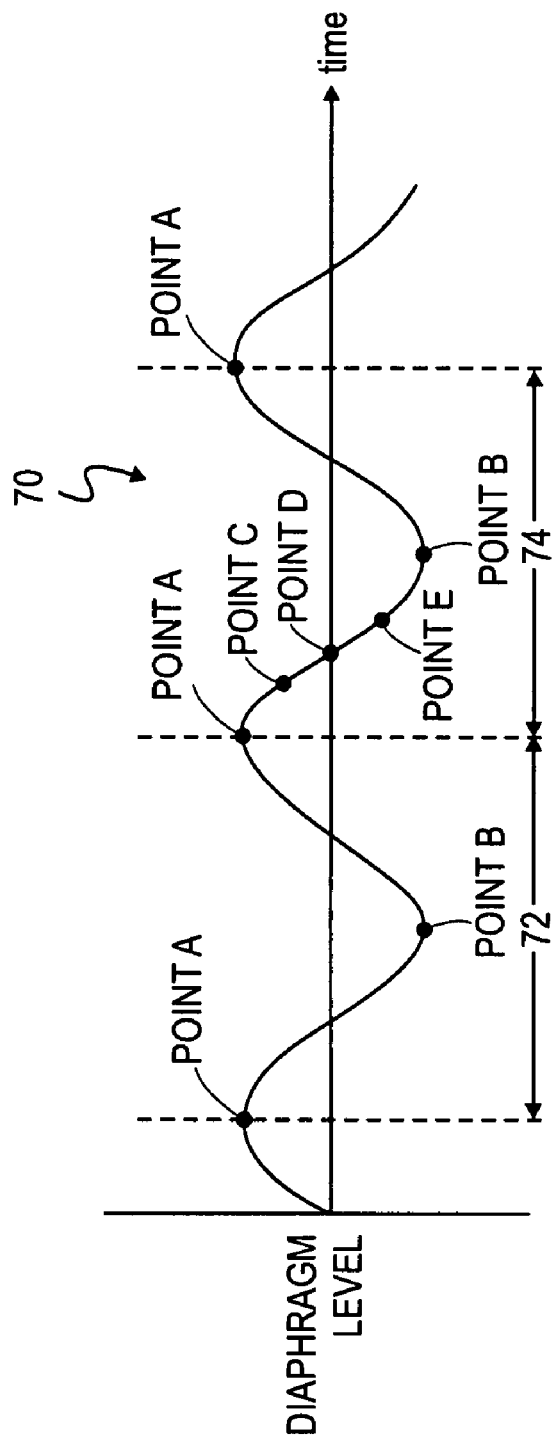
FIG. 3 depicts a respiration pattern including a plurality of respiration cycles.

FIG. 3 depicts a plot 70 of a patient's respiration pattern. The depicted portion of the respiration pattern includes two respiratory cycles, namely cycle 72 and cycle 74. A single respiratory cycle includes the entire range of diaphragm and chest wall movement in the respiration pattern. Thus, point A to point B is one respiration cycle, as is from point B to point B. Since each respiration cycle is substantially similar to one another, point B in respiration cycle 72 is associated with substantially similar internal anatomy as point B in respiration cycle 74. Hence, unless the patient moves, the target region is in a substantially same location at each point A and in a substantially same location at each point B. Also, the target region shifts from the position that it is in at point A to the position that it is in at point B in substantially the same manner in every cycle. Thus, it is possible to produce a set of images of the relevant volume such that there is an image that represents the actual position of the relevant volume at almost every point in a patient's respiratory pattern. Such respiratory pattern represents the individual anatomy of each patient. Some patient training for regular breathing may be required to maximize the reproducibility.

Since a patient's respiratory pattern is substantially cyclical, the processor 12 (see FIG. 1) may be programmed to issue a particular command at one or more preselected points in the respiratory pattern. For example, the processor 12 may be programmed so that CT scans are taken at certain points in the respiratory pattern. This programmed CT scanning may include two general steps: determining the respiratory pattern of a patient and programming the processor 12 to trigger the CT scanner at certain points in this respiratory pattern. For the first step, the respiratory pattern of a patient may be established by using any of the well-known methods or tools, such as the real-time sensing system shown in FIG. 1. Real-time sensors 42 (see FIG. 1), which emit signals indicating the movements of a body part (e.g., chest wall), are coupled to the patient's body. After a critical number of signals are received, the signals are processed to reveal a respiratory pattern.

For the second step, certain points on the pattern are selected based on the number of CT scans that is desired, and the processor 12 is programmed to trigger the CT scanner at the selected points. For example, a first CT scan may be taken at point A, a second CT scan may be taken at point B, and three CT scans may be taken at an equal time interval between point A and point B, resulting in a total of five CT scans that are taken at different points in the respiratory cycle. More specifically, the three CT scans between point A and point B may be taken at points C, D, and E shown in FIG. 3. Alternatively, the points on the pattern may be selected based on the position of a body part that is being tracked. In this case, a first CT scan may be taken at a point when the chest wall is at its highest level, a second CT scan may be taken when the chest wall is a distance Δd below the highest level, a third CT scan may be taken when the chest wall is a distance 2Δd below the highest level, and so on. A person of ordinary skill in the art would understand that this respiratory pattern-based triggering method is not limited to being used with a CT scanner, and that the processor 12 may issue a command to a different device or execute a set of instructions itself. For example, the processor 12 may trigger the CT scanner at point A and point B, and generate synthetic images of the scanned relevant volume for other points in the respiratory cycle between point A and point B.

This method of selecting certain points on the respiratory pattern and programming processor 12 to trigger the CT scanner at the selected points is not limited to being used in the context of radiosurgery. For example, this method can be used to improve conventional CT scans, the quality of which are known to be adversely affected by patient movement (e.g., movement due to respiration). This method allows one to obtain improved three-dimensional images that are free of artifacts of movement, for example for the purpose of diagnosis. When a CT scan is taken using this method, it is clearly known at what point in the respiratory cycle the CT scan is taken.

Figure 4A:
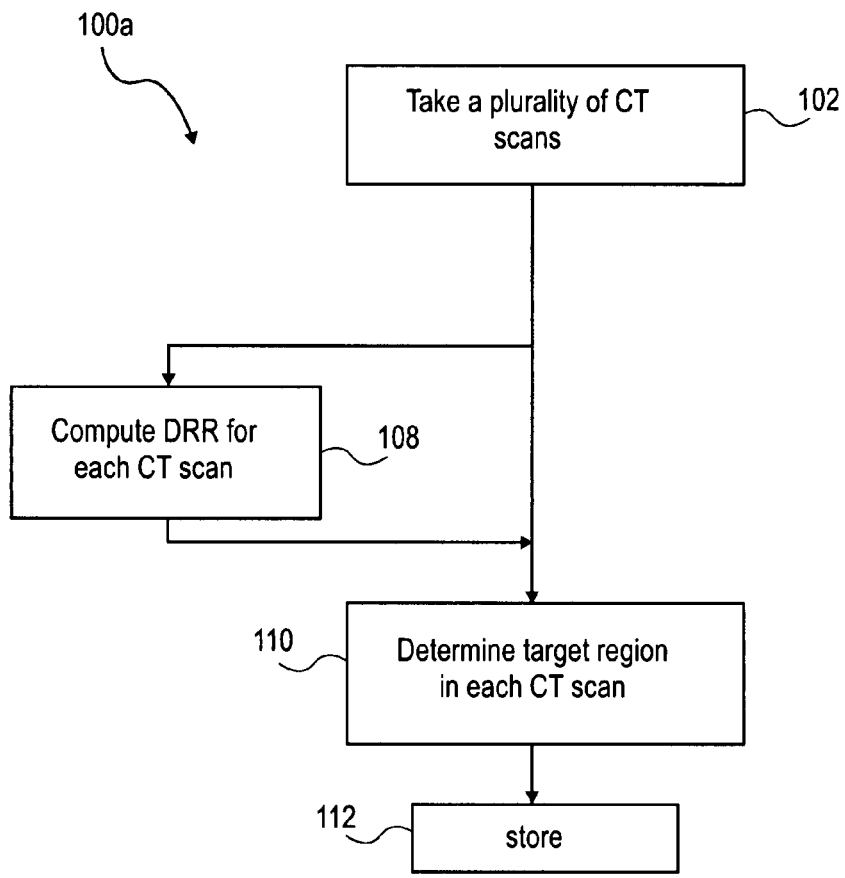
FIG. 4A is a flow chart of a pre-treatment procedure that is executed before real-time tracking of a target region in accordance with the invention.
Figure 4B:
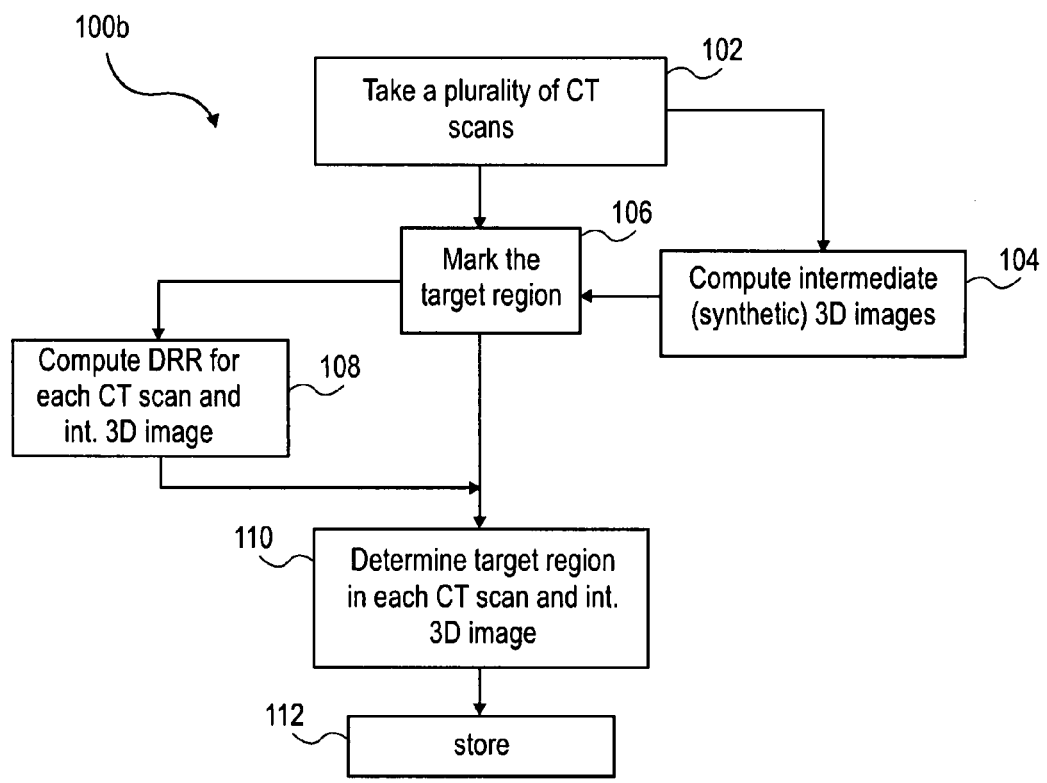
FIG. 4B is a flow chart of an alternative pre-treatment procedure that is executed before real-time tracking of a target region in accordance with the invention.
Figure 7:
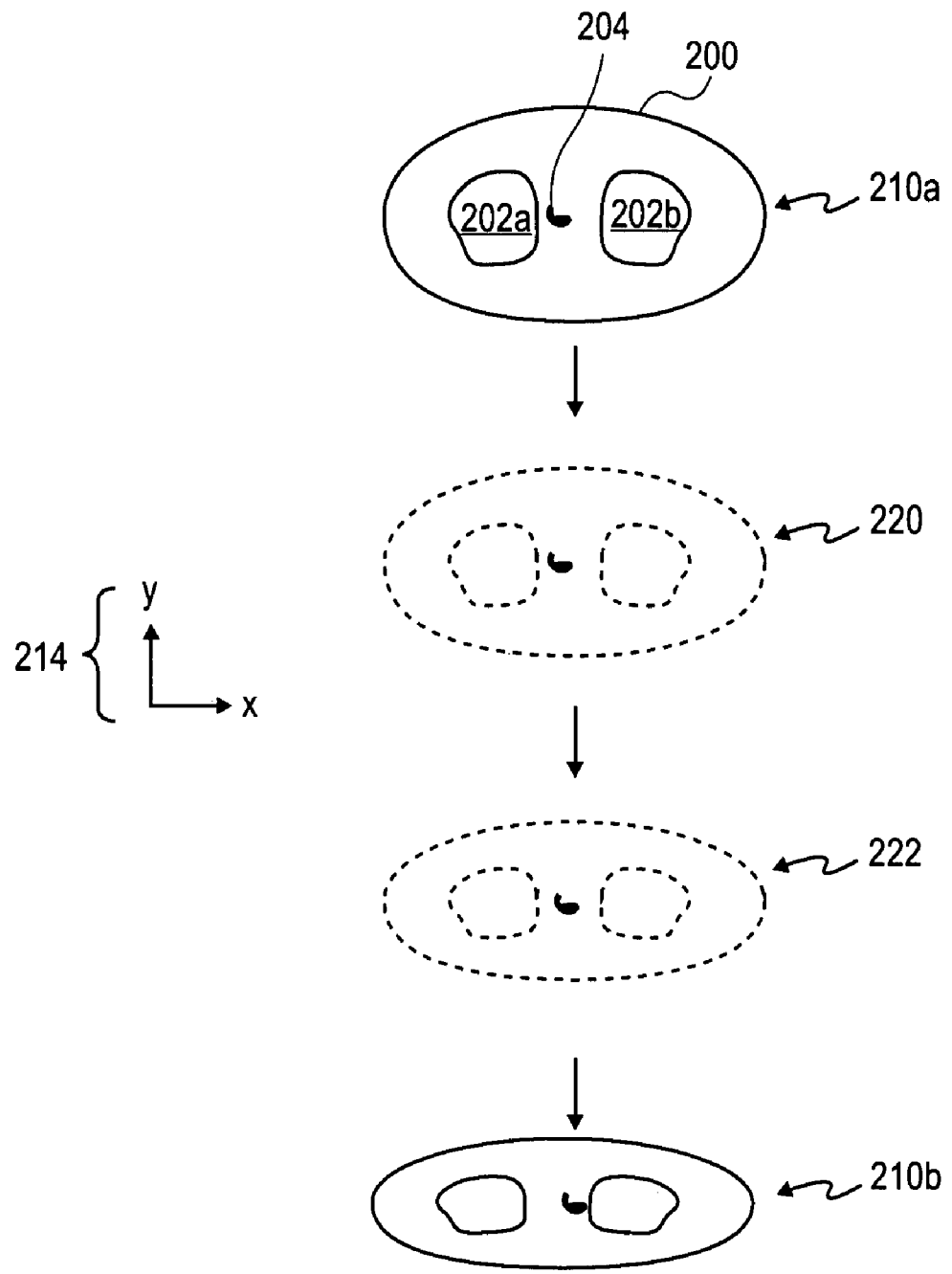
FIG. 7 schematically depicts formation of intermediate three-dimensional images by deformation of a first three-dimensional image into a second three-dimensional image.

The internal location determining process in accordance with the invention includes a pre-treatment procedure 100a and an alternative pre-treatment procedure 100b, one of which is preferably performed prior to the radiation treatment. FIG. 4A and FIG. 4B each depicts this pre-treatment procedure 100a and alternative pre-treatment procedure 100b, respectively. FIG. 5 and FIG. 6 schematically illustrate exemplary three-dimensional images obtained during the pre-treatment procedure 100a, 100b. FIG. 7 schematically illustrates a deformation process that may be used to generate some of the three-dimensional images in the alternative pre-treatment procedure 100b.

FIG. 4A is a flowchart of a pre-treatment procedure 100a that is executed before a treatment for determining the location of a target region in accordance with the invention. The pre-treatment procedure 100a begins when a patient undergoes a plurality of CT scans to produce three-dimensional images that show the patient's relevant volume (i.e., bones, soft tissue, and the target region) at different points in his respiratory cycle (stage 102). The CT scans, each of which shows the target region, may be taken in the manner described above in reference to FIG. 3. The target region position is determined for each of these CT scans (stage 110) and stored (stage 112). In addition, a set of DRRs are generated for each CT scan, each DRR representing the way the relevant volume looks from a particular angle.

In more detail, each CT scan taken in stage 102 represents the patient's internal volume at a specific point in his respiratory cycle. For example, if exactly two CT scans are taken, the first CT scan may be taken at point A in the respiratory cycle and the second CT scan may be taken at point B. Where the relevant volume is near a lung or a liver, point A and point B may be, for example, the points of maximum and minimum inhalation in the patient's respiratory cycle. The position of the target region is identified in each of these CT scans (stage 110), for example as coordinates in the treatment room. Then, the identified position is stored (stage 112) in the memory 13 of the radiation treatment device 10 (see FIG. 1). A person of ordinary skill in the art will understand that although the pre-treatment procedure 100 is described as including CT scans, the CT scans may be replaced by other three-dimensional images that show the bones and tissues of the relevant volume, such as magnetic resonance (MR) images or ultrasound images.

Since the patient may shift his body during treatment, obtaining views of the target region from different angles is important for enhancing the accuracy with which the target region position is determined. In order to take into account any shifting done by the patient during treatment, each of the CT scans is used to generate a set of digitally reconstructed radiographs (DRRs) (stage 108). Each DRR is an image obtained by computing a two-dimensional projection through a three-dimensional image. Thus, a DRR is a synthetic image obtained by computation. A two-dimensional projection through the three-dimensional CT scan resembles the physical process of taking an x-ray image. Thus, a DRR looks similar to an x-ray image. In fact, if the DRR is taken from exactly the same angle as a corresponding x-ray image, the resemblance will be rather close. In this embodiment, each DRR is a synthetic two-dimensional image that shows what the three-dimensional images prepared in stages 102 and 104 look like from a particular angle.

A set of DRRs, all computed from one three-dimensional image but from different angles, resemble a set of x-ray images taken from these angles. Thus, preferably, the DRRs show the target region from a set of angles from which the x-ray generators 32a, 32b (see FIG. 1) view the target region. As the patient may voluntarily or involuntarily shift his body during treatment, DRRs are needed to show what the relevant volume looks like from different angles. Preferably, there are enough DRRs in a set such that there is a DRR that corresponds to almost every position that the patient 14 can shift into during treatment, and a set of DRRs may include as many DRRs as a person of ordinary skill in the art deems adequate.

FIG. 4B depicts an alternative pre-treatment procedure 100b in accordance with the invention. This alternative pre-treatment procedure 100b is similar to the pre-treatment procedure 100a of FIG. 4A except that the three-dimensional images are a combination of actual CT scans and computer-generated intermediate three-dimensional images. In stage 102, a plurality (e.g., two) CT scans are taken of the relevant volume at point A and point B of the respiratory cycle. These CT scans are then used to compute a series of intermediate three-dimensional images (stage 104) by computing synthetic deformation images from the actual CT scans taken during stage 102. Each of the intermediate three-dimensional images shows the position of the target region at a respiratory state between point A and point B. The computation for producing these intermediate three-dimensional images may be performed offline, by any of the well-known methods such as thin-plate splines, warping, interpolation, or extrapolation. The position of the target region is marked in each of these CT scans and intermediate three-dimensional images (stage 106). This marking may also be done offline. Both the CT scans taken in stage 102 and the intermediate three-dimensional images taken in stage 104 are herein referred to as "three-dimensional images."

In one exemplary embodiment, two CT scans are obtained in stage 102 and ten intermediate three-dimensional images are produced in stage 104. Then, for each of these three-dimensional images, forty DRRs are generated in stage 108. Since there are twelve three-dimensional images total, this means that a total of 480 DRRs are generated. Put another way, each three-dimensional image representing a point in the respiratory cycle is viewed from 40 different angles. As described below in reference to FIG. 8, the DRRs are used to match up a live x-ray image with a three-dimensional image, which is in turn used to determine the position of the target region.

FIG. 5 schematically depicts a CT scan 210a that is taken at point A of the respiration cycle in stage 102 of the pre-treatment procedure 100. FIG. 6 depicts a CT scan 210b taken at point B of the respiration cycle, also in stage 102 of the pre-treatment procedure 100. Specifically, FIGS. 5 and 6 show a cross sectional view of a relevant volume 200, soft tissues 202a and 202b, and a target region 204 located between soft tissues 202a and 202b. The soft tissues 202a and 202b are aligned in the x-direction according to a coordinate system 214. At point A in the respiration cycle, the target region 204 is located closer to soft tissue 202a than to soft tissue 202b, as shown in FIG. 5. At point B in the respiration cycle, however, the target region 204 is closer to soft tissue 202b than to soft tissue 202a, as shown in FIG. 6. Thus, the target region 204 was displaced along the x-direction between point A and point B of the respiration cycle. Also, the shape of the relevant volume 200 is different in FIG. 6 than in FIG. 5. More specifically, the relevant volume 200 and the soft tissues 202a and 202b shrank along the y-direction in going from point A (depicted in FIG. 5) to point B (depicted in FIG. 6) in the respiration cycle. Thus, in going from point A to point B in the respiration cycle, the relevant volume 200 shrinks along the y-direction and the target region 204 is displaced along the x-direction.

FIG. 7 schematically depicts the generation of intermediate three-dimensional images in stage 104 of FIG. 4B. Two exemplary intermediate three-dimensional images 220 and 222 are generated based on two CT scans 210a and 210b. The three-dimensional images 220 and 222 are formed by continuously deforming the CT scan 210a taken at point A of the respiration cycle into the CT scan 210b taken at point B. Thus, the three dimensional images 220 and 222 depict the intermediate stages the relevant volume 200 and the target region 204 go through while transitioning from point A to point B in the respiration cycle. As previously mentioned in reference in FIG. 3, point A is the point of maximum inhalation and point B is the point of maximum exhalation for the purpose of illustration herein. Thus, the relevant volume 200 becomes progressively smaller along the y-direction and the target region 204 becomes progressively closer to soft tissue 202b as the patient 14 exhales.

Figure 8:
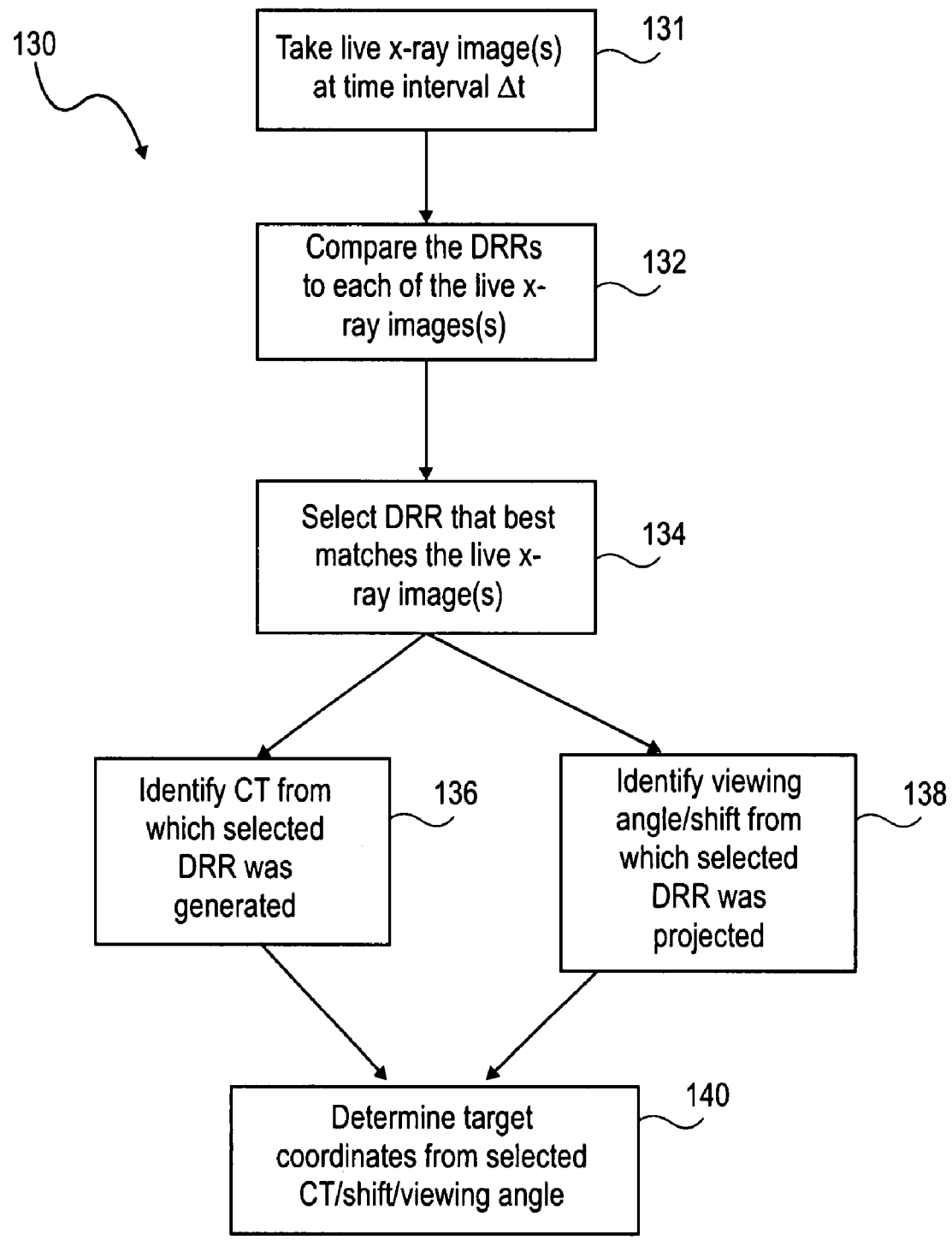
FIG. 8 is a flow chart depicting a fiducial-less target tracking procedure for determining a target position during treatment without an implanted fiducial.

FIG. 8 is a flow chart depicting a fiducial-less target tracking procedure 130, which allows the position of the target region to be determined without implanted fiducials in accordance with the invention. During treatment, live stereo x-ray images are taken periodically, at time interval Δt (stage 131). Since the x-ray imaging themselves do not show the target region, the live x-rays have to be associated with a proper three-dimensional image in order for the position of the target region to be determined. Each of these x-ray images are compared to the DRRs prepared during the pre-treatment procedure 100a, 100b (stage 132). Since the x-ray images do not show everything in the relevant volume that the three-dimensional images show (e.g., the target region), what is matched are the positions of the parts of the relevant volume that show up in both the x-ray images and the DRRs. This comparison may be made by processor 12 for each live x-ray image, using any well known image comparison technique including but not limited to mutual information, cross correlation, and image subtraction. With one of these techniques, each DRR and the live x-ray image are compared pixel by pixel. This comparison may entail subtracting the gray level pixel values in both images for each pixel location. The accumulated differences in gray levels give an error signal characterizing the distance between the DRR and the x-ray image. A person of ordinary skill in the art would understand how to implement a suitable comparison technique.

Through this comparison, a DRR that best matches the x-ray image(s) is selected (stage 134). Since every DRR is associated with a three-dimensional image, the associated three-dimensional image is identified (stage 136). In addition, the correct angle associated with the best-matching DRR must be identified (stage 138). Based on the identified three-dimensional image and viewing angle, target region position is determined (stage 140). Then, the viewing angle is added to this target position (also stage 140). Once the position of the target region as seen from the angle of the x-ray imaging devices is known, the position of the target region can be determined accurately. The location of the target region is then inferred and determined with respect to the treatment room coordinates (stage 128). Since the respiratory pattern is substantially cyclical, the location of the target region can even be predicted after a critical number of data points are taken.

Although the fiducial-less procedure 130 of FIG. 8 affords the significant advantage of locating a target region without implanted fiducials, it does not allow real time tracking because x-ray imaging alone may be too slow for detecting fast respiration. The time interval Δt at which x-ray images are taken may be as long as 10 seconds since too frequent of x-ray imaging could expose the patient to excess radiation. Locating the target region every 10 seconds does not provide accurate beam directing because the target region can move out of the beam radius within 10 seconds. The treatment beam needs to be adjusted between the x-ray images, at a time interval that is shorter than Δt. In order to achieve a closer tracking of the target region, easily trackable real-time sensors may be implemented to provide measurement data in real time, i.e., with negligible lag time between a movement of the patient's body part and the "reporting" of the movement. Determining the location of the target region based on the position of the real-time sensors allows a real-time determination of the location of the target region. Since the use of real-time sensors is non-invasive, cheaper, and overall much less complicated than the use of internal fiducials, the ability to determine the position of the tumor based on real-time sensors without using internal fiducials is desirable.

In order to overcome the slowness of x-ray imaging that makes real-time tracking difficult, real-time sensors may be used in conjunction with the fiducial-less target tracking procedure 130. In order for the real-time sensors to be used with fuducial-less target tracking procedure 130 to locate the target region real-time, a correlation has to be established between real-time sensors and the position of the target region.

Figure 9:
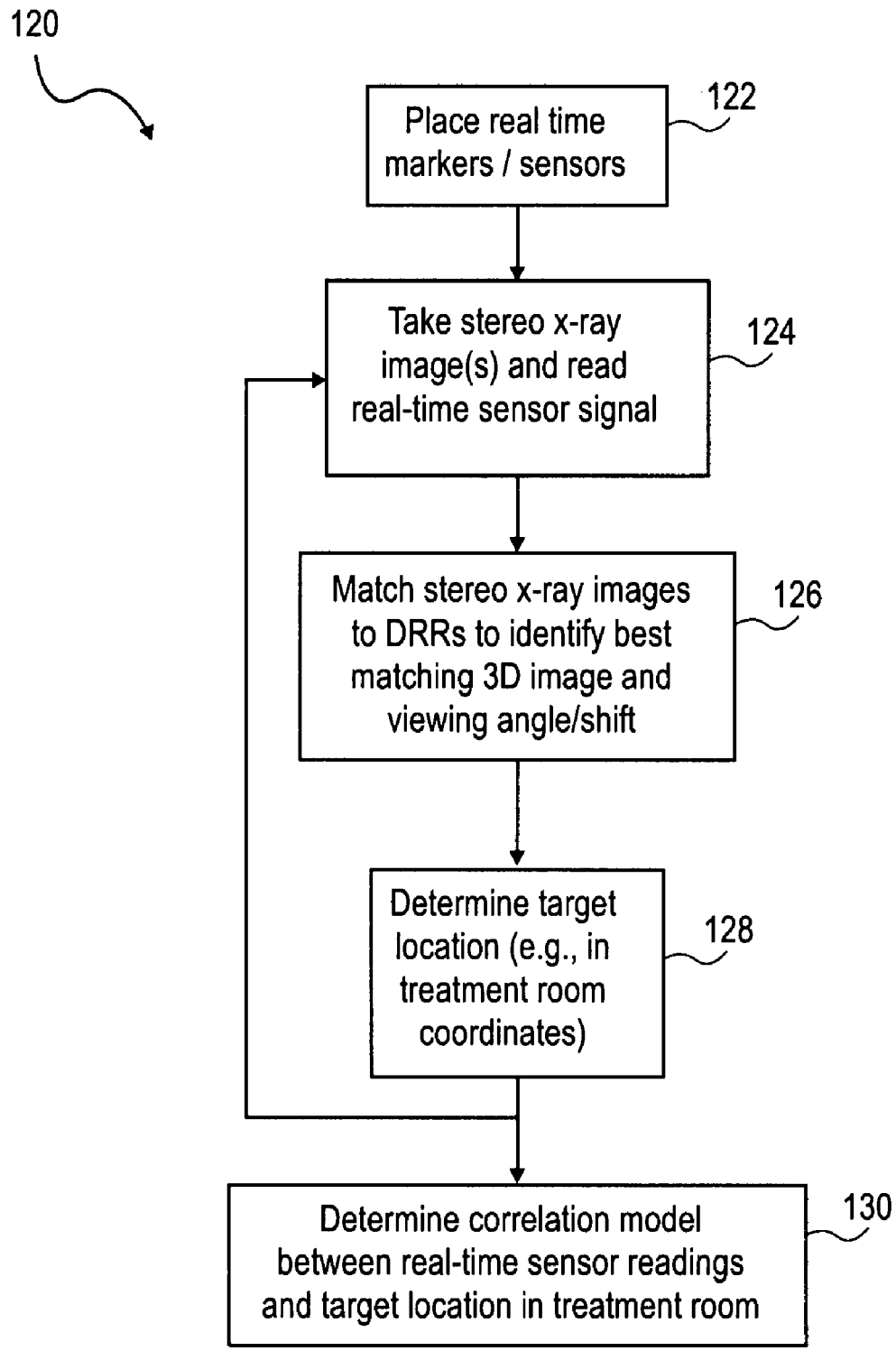
FIG. 9 is a flow chart depicting a correlation process for correlating a real-time sensor readings to target positions.

FIG. 9 is a flow chart depicting a sensor-target region correlation procedure 120 which is a procedure for establishing a correlation model between real-time sensor readings and the position of the target region. In a treatment room, the patient is placed on the tilting top 38 (see FIG. 1) within the view of at least two x-ray generators 32a, 32b (see FIG. 1). For real-time target tracking, a real time sensor may be coupled to an external body part (e.g., the skin) of the patient, or activated (stage 122) after the patient 14 is placed in the treatment room. As described above in reference to FIG. 1, this real-time sensor may be any sensor showing a correlation to respiration with response or reactivation time of less than 250 ms. In addition, the real-time sensor should emit a new signal at least ten times per second. The signal from the real-time sensor can be read at a time interval $\Delta t_{sensor}$ that is shorter than Δt. Then, a stereo x-ray image is taken (stage 124). At the same time the x-ray image is taken, the signal from the real-time sensor is read, and the reading may be time-stamped. Stage 124 is repeated at a time interval Δt. Sensor reading interval $\Delta t_{sensor}$ does not have to be absolutely constant as long as each consecutive sensor readings are taken sufficiently closely in time (i.e., $\Delta t_{sensor}$ is small enough). The same holds for x-ray imaging.

The stereo x-ray image is then compared with the DRRs that were obtained during the pre-treatment procedure 100a, 100b (stage 126). The comparison identifies the best matching DRR which points to a three-dimensional image from which this DRR was generated. Since the position of the three-dimensional image was marked during the pre-treatment procedure, the position of the target region is determined from the three-dimensional image (stage 128). Using the determined target region positions, the data points collected in stage 124 can be converted into data points of the target region position and corresponding real-time sensor readings, producing a point cloud. The processor 12 (see FIG. 1) in the radiosurgery device may fit a first curve to the points generated by the real-time sensors and a second curve to the points generated for the target position. These curves permit the real time sensor readings and target position to be correlated to each other (stage 130) to produce a correlation model that is eventually used during treatment to track the target region.

Another way to perform the correlation of the position of the target region position and the real-time sensor(s) is to use a neural network trained to perform interpolation or other known mathematical interpolation methods for establishing the correspondence between two sets of data after having computed the point clouds.

Figure 10:
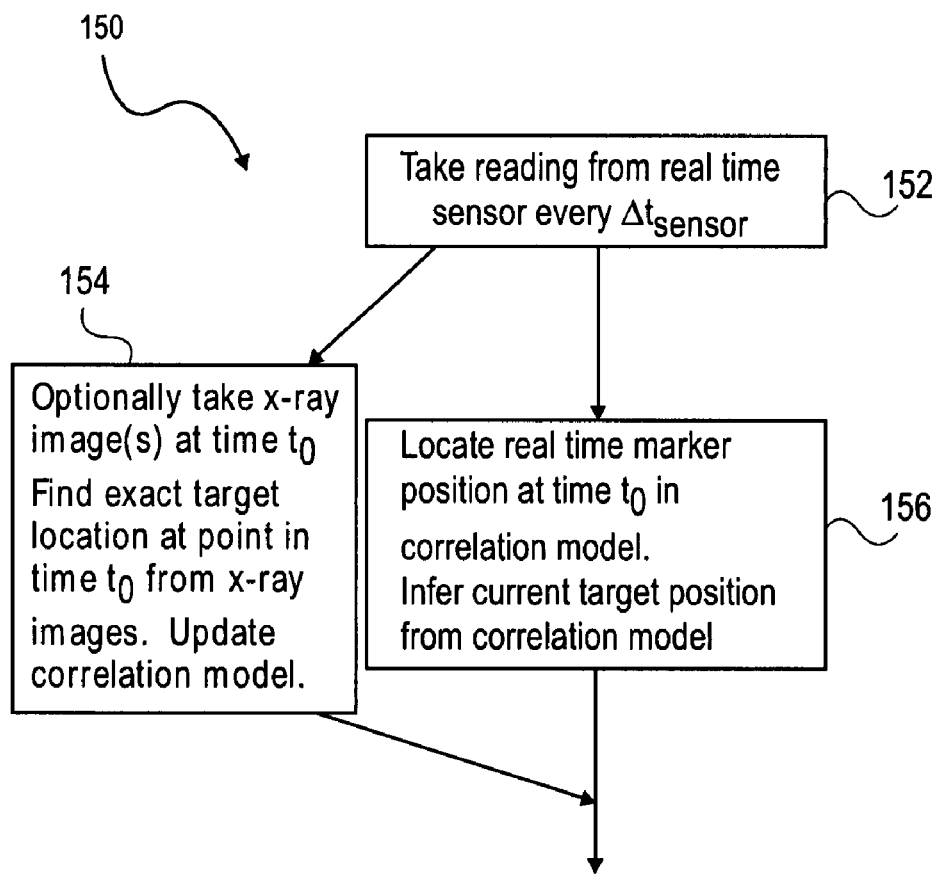
FIG. 10 is a flow chart depicting the real time tracking procedure for the real time tracking of the target region during treatment.

FIG. 10 depicts the real time tracking procedure 150 for the real-time tracking of the target region during treatment. The real time tracking procedure 150 begins with taking a reading from a real-time sensor at times $t_{sensor\ 1}$, $t_{sensor\ 2}$, $t_{sensor\ 3}$, ... each separated by a time interval that is not necessarily constant (stage 152). For clarity of illustration, the time interval herein is expressed as time interval $\Delta t_{sensor}$ wherein $\Delta t_{sensor}$ is a range of time rather than an exact and constant value. As the real-time sensor signal can be read more frequently than the interval at which x-ray images are taken ($\Delta t > \Delta t_{sensor}$), real-time sensor information can be acquired between successive x-ray images. $\Delta t_{sensor}$ may be, for example 50 ms, while $\Delta t$ may be 10 seconds.

The system reads a signal s from the real-time sensor at time $t_{sensor\ 1}$. No x-ray image is taken at time $t_{sensor\ 1}$. Then, the position of the target region at time $t_{sensor\ 1}$ is obtained based on this real-time sensor reading s (stage 156) based on the correlation between the real-time sensor reading and the position of the target region that was established during the sensor-target region correlation procedure 120. More specifically, the signal s is fit to the previously generated first curve of the real-time sensor readings. Next, a position y of the target region that corresponds to the sensor signal s is determined by identifying a point on the second curve that corresponds to the position of s on the first curve, or by a well-known interpolation method. If there are multiple real-time sensors, this process may be performed for each real-time sensor. This way, the position of each real-time sensor that was obtained in stage 152 is matched to one of the real-time sensor readings in the correlation model, and the position of the target region is inferred from the real-time sensor reading.

As previously mentioned, the real-time sensor signals are read frequently (e.g., every 50 ms). Based on the sensor-target position correlation, the position of the target region to be determined as frequently as the sensor signals are read. Thus, with the present invention, it is not necessary to actually image the internal target region on a real-time basis in order to track the target region almost continuously.

Optionally, a live x-ray image may be taken at time $t_0$ (stage 154), when the signal s is read from the real-time sensors. Preferably, the x-ray time interval $\Delta t$ is a multiple of the sensor reading time interval $\Delta t_{sensor}$ so that after a certain number of sensor readings, the x-ray imaging and the sensor reading occurs simultaneously. This new x-ray image, which is an additional data point, may be added to the point cloud and be used to modify or update the correlation model. This constant updating prevents any change in respiratory pattern during treatment from compromising the accuracy of the treatment.

It should be noted that the invention is not limited to a specific number of sensors or sensors that track respiratory motion. The number of sensors to be used may be determined based on the degree of accuracy or certainty that is desired. Multiple sensors can lead to multi-level correlation, enhancing the reliability and accuracy of tracking. In one embodiment, three sensors may be used: a first sensor that is read at a time interval of $\Delta t_{sensor}$, a second sensor that is read at a time interval $\Delta t$, and a third sensor that is read at another time interval between $\Delta t_{sensor}$ and $\Delta t$. The extra sensor(s) may track a patient motion that is caused by something other than respiration and that also moves the target region. For example, aortic pulsation or heart cycles may be tracked to take into account the movement of the target region due to the motion of the heart. If the motion being tracked by the extra sensor(s) is cyclical, it can be handled in a manner similar to the manner in which motion due to respiration is handled. If desired, sensor(s) may be used to track only motions other than respiratory motion.

This invention allows real-time tracking of the target region during treatment based on the location of the real-time sensors. In addition, this invention allows the target region to be tracked during treatment based only on x-ray images. The x-ray image is obtained when the position of the real-time sensors is determined. Further, each DRR is associated with an intermediate three dimensional image prior to the treatment. Thus, the only task processor 12 needs to perform during treatment is finding the DRR that best matches the x-ray that is just taken. The simplicity of the task and the short process time minimizes the time lag between when processor 12 determines the location of the target region and when the beaming apparatus 20 (see FIG. 1) physically adjusts its beam direction according to the new location of the target region. Meanwhile, tracking of the markers is so frequently done that the treatment beam may be adjusted almost continuously to ensure that it is accurately aimed at the target region during the entire span of the treatment. As tracking the markers is noninvasive and inexpensive, the invention allows a noninvasive and inexpensive alternative to improving the accuracy of radiation treatments.

While the foregoing has been with reference to a particular embodiment of the invention, it will be appreciated by those skilled in the art that changes in this embodiment may be made without departing from the principles and spirit of the invention, the scope of which is defined by the appended claims.

What is claimed is:

1. A method for locating an internal target region during treatment, the method comprising:
   generating a plurality of first images of a relevant volume of a patient, the relevant volume including the internal target region and each of the plurality of first images showing the internal target region;
   generating a live image of the relevant volume at a predetermined time during treatment; and
   determining a location of the internal target region at the predetermined time by identifying one of the plurality of first images that best matches the live image.

2. The method of claim 1, wherein the plurality of first images include one of computer tomography scans, ultrasound images, and magnetic resonance images.

3. The method of claim 1, wherein the plurality of first images are three-dimensional images.

4. The method of claim 1, wherein generating the plurality of first images comprises:
   generating a first computer tomography scan taken at a first point of a respiratory cycle;
   generating a second computer tomography scan taken at a second point of the respiratory cycle; and
   generating at least one computer-generated intermediate three-dimensional image depicting the relevant volume at a third point between the first point and the second point.

5. The method of claim 4, wherein generating the at least one intermediate three-dimensional image comprises interpolating between the first computer tomography scan and the second computer tomography scan and modifying one of the first and the second computer tomography scans.

6. The method of claim 4, wherein generating the at least one intermediate three-dimensional image comprises continuously deforming a first three-dimensional image into a second three-dimensional image taken at a different point in time from the first three-dimensional image.

7. The method of claim 1, wherein the plurality of first images are generated at preselected points in the patient's respiratory pattern.

8. The method of claim 1, further comprising computing a plurality of digitally reconstructed radiographs for each of the plurality of first images, wherein each of the plurality of digitally reconstructed radiographs represents the relevant volume from a particular viewing angle.

9. The method of claim 8, wherein each of the first images indicate a point in the respiratory cycle and each of the digitally reconstructed radiographs indicate a rotational and translational shift of the relevant volume.

10. The method of claim 8, wherein identifying one of the plurality of first images that best matches the second image comprises comparing the digitally reconstructed radiographs to the second image.

11. The method of claim 10, wherein the comparing comprises comparing the digitally reconstructed radiographs and the second image on a pixel by pixel basis.

12. The method of claim 1, wherein the second image comprises an x-ray image.

13. The method of claim 1, wherein generating the plurality of first images is done independently of the generating of the second image.

14. The method of claim 1, wherein the plurality of first images is generated prior to treatment and the second image is a live image generated during treatment.

15. The method of claim 1, wherein the position of the internal target region is indicated in coordinates of a treatment room.

16. The method of claim 1, further comprising: coupling a real-time sensor to an external body part of the patient, the real-time sensor being read at time interval $\Delta t_{sensor}$;
reading a signal s from the real time sensor and generating a corresponding image of the relevant volume simultaneously at a time interval $\Delta t$ wherein $\Delta t$ is greater than $\Delta t_{sensor}$; and identifying one of the plurality of first images that best matches the corresponding image to generate a correlation between the position of the target region and the signal.

17. The method of claim 16, wherein generating the correlation comprises: reading the signal and generating the corresponding image of the relevant volume at a plurality of different points in time to produce a set of signal data and a set of corresponding image data;
fitting a first curve through the set of signal data;
fitting a second curve through the set of corresponding image data; and
comparing the first curve and the second curve.

18. The method of claim 17, further comprising:
reading the signal s from the real-time sensor at a time $t_{sensor}$;
locating the signal s on the first curve; and
inferring the position of the target region at time $t_{sensor}$ by identifying a point y on the second curve that corresponds to the signal s of the first curve.

19. The method of claim 17, further comprising:
periodically taking a new x-ray image of the relevant volume and simultaneously reading a corresponding signal during treatment; and
updating the correlation with the new x-ray image and the corresponding signal.

20. The method of claim 16, wherein the real-time sensor comprises one of infrared tracking, force sensors, air flow meters, strain gauges, laser range sensors, and a variety of sensors based on haptic, acoustic, ultrasound, magnetic, mechanical and optical principles.

21. The method of claim 16, wherein the real-time sensor is a first sensor, further comprising coupling one or more additional sensors to the patient's body to track patient motion.

22. The method of claim 1, further comprising:
determining a respiratory pattern of the patient; and
predicting the location of the target region at a future point in time based on the respiratory pattern and the plurality of first images that are taken at different points in the respiratory pattern.

23. An apparatus for tracking the location of an internal target region inside a patient, the apparatus comprising:
an imaging device configured to generate a live image of a relevant volume that includes the internal target region;
a memory unit storing a plurality of three-dimensional images wherein each of the three-dimensional images shows a pre-generated image, generated prior to treatment, of the relevant volume and the internal target region; and
a processor coupled to the imaging device and the memory unit, the processor including a first set of computer-readable instructions for selecting a best three-dimensional image that most closely resembles the live image and a second set of computer-readable instructions for determining a position of the internal target region at the time the live image is generated based on the best three-dimensional image.

24. The apparatus of claim 23 further comprising a plurality of digitally reconstructed radiographs stored in the memory unit, wherein each one of the plurality of digitally reconstructed radiographs is associated with one of the plurality of three-dimensional images, and wherein the processor uses the digitally reconstructed radiographs to select the best three-dimensional image.

25. The apparatus of claim 24 wherein each of the plurality of digitally reconstructed radiographs reflects a different displacement of the relevant volume that results from a patient's shifting his body.

26. The apparatus of claim 23, wherein the plurality of three-dimensional images include one of a computer tomography scan, a magnetic resonance image, and an ultrasound image.

27. The apparatus of claim 23, wherein the plurality of three-dimensional images includes a first three-dimensional image, a second three-dimensional image, and at least one synthetic three-dimensional image generated by interpolating between the first and the second three-dimensional images and modifying one of the first and second three-dimensional images.

28. The apparatus of claim 23, wherein the imaging device comprises at least one x-ray generator and the live image is a stereo x-ray image.

29. The apparatus of claim 28 further comprising a sensing system coupled to the processor, the sensing system reading a movement of an external body part at the same time that the imaging device generates a live image so that the processor generates a correlation between the movement of the external body part and the position of the target region.

30. The apparatus of claim 29, wherein the sensing system comprises one of infrared tracking, force sensors, air flow meters, strain gauges, laser range sensors, and a variety of sensors based on haptic, acoustic, ultrasound, magnetic, mechanical and optical principles.

31. The apparatus of claim 23 further comprising a respiratory pattern of the patient stored in the memory unit, wherein processor comprises a third set of computer-readable instructions for generating a three-dimensional image of the relevant volume at one or more preselected points in the respiratory pattern.

32. The apparatus of claim 23 further comprising a beaming device directing a treatment beam to the location of the target region in response to a processor command.

33. The apparatus of claim 23 wherein the plurality of three-dimensional images comprises at least one of a computer tomography scan, a magnetic resonance image, or an ultrasound image.

34. An apparatus for tracking the location of a target region inside a patient, the apparatus comprising:
  means for generating a plurality of first images of a relevant volume inside the patient, the relevant volume including the target region and each of the plurality of first images showing the target region;
  means for generating a live image of the relevant volume at a predetermined time during treatment; and
  means for determining a location of the internal target region at the predetermined time by identifying one of the plurality of first images that best matches the live image.

35. The apparatus of claim 34, wherein the means for generating the plurality of first images comprises:
  means for generating a first computer tomography scan taken at a first point of a respiratory cycle;
  means for generating a second computer tomography scan taken at a second point of the respiratory cycle; and
  means for generating at least one computer-generated intermediate three-dimensional image depicting the relevant volume at a third point between the first point and the second point.

36. The apparatus of claim 35, wherein the means for generating the at least one intermediate three-dimensional image comprises means for interpolating between the first computer tomography scan and the second computer tomography scan and modifying one of the first and the second computer tomography scans.

37. The apparatus of claim 34, further comprising means for computing a plurality of digitally reconstructed radiographs for each of the first images, wherein each of the plurality of digitally reconstructed radiographs is a representation of the relevant volume from a particular viewing angle.

38. The apparatus of claim 37, wherein the means for identifying one of the plurality of first images comprises means for comparing the digitally reconstructed radiographs to the live image.

39. The apparatus of claim 34, further comprising:
  means for sensing a movement of an external body part of the patient, the means for sensing emitting a signal at time interval $\Delta t_{sensor}$;
  means for reading the signal and generating a corresponding image of the relevant volume simultaneously at a time interval $\Delta t$ wherein $\Delta t$ is greater than $\Delta t_{sensor}$; and
  means for identifying one of the plurality of first images that best matches the corresponding image to generate a correlation between the position of the target region and the signal.

40. The apparatus of claim 39, wherein the means for identifying comprises: means for reading the signal and generating the corresponding image of the relevant volume at a plurality of different points in time to produce a set of signal data and a set of corresponding image data;
  means for fitting a first curve though the set of signal data;
  means for fitting a second curve though the set of corresponding image data; and
  means for comparing the first curve and the second curve.

41. The apparatus of claim 40, further comprising:
  means for reading a signal s from the real-time sensor at a time $t_{sensor}$;
  means for locating the signal s on the first curve; and
  means for inferring the position of the target region at time $t_{sensor}$ by identifying a point y on the second curve that corresponds to the signal s of the first curve.

42. The apparatus of claim 40, further comprising:
  means for periodically taking a new x-ray image of the relevant volume and simultaneously reading a corresponding signal during treatment; and
  means for updating the correlation with the new x-ray image and the corresponding signal.

43. A method for locating during treatment an internal target region in a patient who is undergoing a motion, the method comprising:
  generating prior to treatment a plurality of first images of a relevant volume of a patient, the relevant volume including the target region and each of the plurality of first images showing the target region;
  generating a second image of the relevant volume at a predetermined time during treatment; and
  determining a location of the target region at the predetermined time by identifying one of the plurality of first images that best matches the second image.

44. The method of claim 43, wherein the motion of the patient comprises periodic respiratory motion characterized by a respiratory cycle, and wherein generating the plurality of first images comprises:
  generating a first computer tomography scan taken at a first point in the respiratory cycle;
  generating a second computer tomography scan taken at a second point of the respiratory cycle; and
  generating at least one computer-generated intermediate three-dimensional image depicting the relevant volume at a third point between the first point and the second point.

45. The method of claim 44, further comprising computing a plurality of digitally reconstructed radiographs for each of the plurality of first images, wherein each of the plurality of digitally reconstructed radiographs represents the relevant volume when viewed from a particular viewing angle.

46. The method of claim 45, wherein each of the first images indicate a position of the target region at a corresponding point in the respiratory cycle and each of the digitally reconstructed radiographs indicate a rotational and translational shift of the target region.

* * * * *